United States Patent [19]
Nakagawa et al.

[11] Patent Number: 5,153,188
[45] Date of Patent: Oct. 6, 1992

[54] PIPERIDYLTHIOCARBAPENEM DERIVATIVES

[75] Inventors: Susumu Nakagawa; Shinji Kato; Hiroshi Fukatsu, all of Aichi, Japan

[73] Assignee: Banyu Pharmaceutical Co., Ltd., Tokyo, Japan

[21] Appl. No.: 561,846

[22] Filed: Aug. 2, 1990

[30] Foreign Application Priority Data

Aug. 2, 1989 [JP] Japan ................................. 1-200805

[51] Int. Cl.$^5$ .................... G07D 487/01; A61K 31/40
[52] U.S. Cl. ..................................... 514/210; 540/350
[58] Field of Search .......................... 540/350; 514/210

[56] References Cited

U.S. PATENT DOCUMENTS 4,757,066  7/1988  Shiokari ............... 514/210
4,888,349 12/1989  Sunagawa .............. 514/210

FOREIGN PATENT DOCUMENTS 0144825  6/1985  European Pat. Off. .
0160391 11/1985  European Pat. Off. .
0161541 11/1985  European Pat. Off. .

*Primary Examiner*—Robert Gerstl
*Attorney, Agent, or Firm*—Sughrue, Mion, Zinn, Macpeak & Seas

[57] ABSTRACT

A compound represented by the general formula (I):

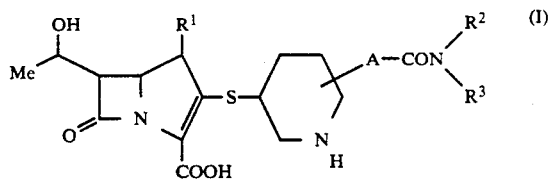

wherein $R^1$ is a hydrogen atom or a methyl group; $R^2$ and $R^3$, which may be the same or different, each represents a hydrogen atom or a lower alkyl group, or taken together with the adjacent nitrogen atom, jointly represent a heterocyclic group selected from the group consisting of an aziridinyl group, an azetidinyl group, a pyrrolidinyl group, a piperidino group, a piperazinyl group, a 4-lower alkylpiperazinyl group, a morpholino group and a thiomorpholino group; and A is a single bond, a lower alkylene group, a lower alkenylene group or a lower alkynylene group; or a pharmaceutically acceptable salt or ester thereof.

The compound of the general formula (I) and their salts or esters exhibit excellent antibacterial activity.

9 Claims, No Drawings

PIPERIDYLTHIOCARBAPENEM DERIVATIVES

FIELD OF THE INVENTION

The present invention relates to a novel carbapenem derivative useful as a therapeutic agent for infectious diseases caused by various bacteria, a process for production of the carbapenem derivative, an antibacterial agent containing the carbapenem derivative, and intermediates for production of the carbapenem derivative.

BACKGROUND OF THE INVENTION

Since thienamycin having useful activities as an antibiotic was discovered, a number of carbapenem derivatives have been synthesized and applied for patents. For example, EP 160,391 (The term "EP" as used herein means an "European patent publication") proposes various alicyclic aminothio groups for the side chain at the 2-position of the carbapenem skeleton. EP 160,391 includes a generalized and categorical statement about alicyclic aminothio groups but as far as can be inferred from the working examples included therein, the technology is directed simply to carbapenem compounds having a 3-pyrrolidinylthio group N-substituted with a substituted imidoyl group or 5-(3,4,5,6-tetrahyiropyrimidinyl)thio group at the 2-position of the carbapenem skeleton. Furthermore, notwithstanding the statement that these carbapenem compounds in general have excellent antibacterial activity, this assertion is not supported by factual antibacterial activity data at all. Particularly, although this literature includes an extensive listing of 122 compounds, only 11 different side chain groups can be identified from the compounds allegedly synthesized in the working examples.

While carbapenem derivatives are useful for the treatment of human and animal diseases caused by pathogenic bacteria, antibacterial activities of the state-of-the-art carbapenem derivatives are not sufficiently satisfactory, and there has been a demand to develop a compound exhibiting excellent antibacterial activity against various pathogenic bacteria.

Imipenem, a carbapenem compound now clinically used, is decomposed by renal dehydropeptidase (hereinafter abbreviated as DHP) similarly to thienamycin, so that it is used in combination with a DHP inhibitor, e.g., cilastatin. Hence, a carbapenem compound having improved stability against DHP as well as satisfactory antibacterial activity has been demanded.

SUMMARY OF THE INVENTION

The inventors have conducted extensive investigations to develop a carbapenem derivative having excellent antibacterial activity against various pathogenic bacteria. As a result, it has now been found that a novel carbapenem derivative represented by the general formula (I) shown below shows excellent antibacterial activity and reached the present invention.

That is, the present invention relates to a compound represented by the general formula (I):

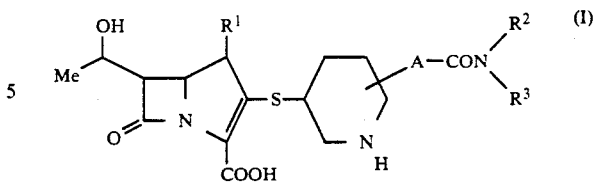

wherein $R^1$ is a hydrogen atom or a methyl group; $R^2$ and $R^3$, which may be the same or different, each represents a hydrogen atom or a lower alkyl group, or taken together with the adjacent nitrogen atom, jointly represent a heterocyclic group selected from the group consisting of an aziridinyl group, an azetidinyl group, a pyrrolidinyl group, a piperidino group, a piperazinyl group, a 4-lower alkylpiperazinyl group, a morpholino group and a thiomorpholino group; and A is a single bond, a lower alkylene group, a lower alkenylene group or a lower alkynylene group; or a pharmaceutically acceptable salt or ester thereof.

The present invention can also relates to a process for producing the compound of the general formula (I) or a pharmaceutically acceptable salt or ester thereof.

The present invention further relates to an antibacterial agent containing the compound of the general formula (I) or a pharmaceutically acceptable salt or ester thereof as an active ingredient.

The present invention furthermore relates to an intermediate compound for use in the production of the present carbapenem derivative, which is represented by the general formula (II):

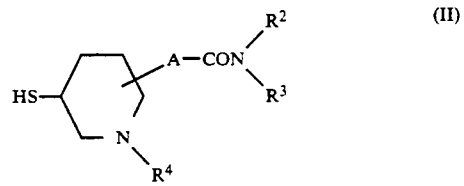

wherein $R^2$, $R^3$ and A are as defined above; and $R^4$ is a hydrogen atom or an imino-protecting group.

DETAILED DESCRIPTION OF THE INVENTION

The terminology "lower" as used herein means that the group following "lower" contains from 1 to 6 carbon atoms. That is, "lower alkyl group" includes methyl, ethyl, n-propyl, isopropyl, n-butyl, isobutyl, t-butyl, n-pentyl, n-hexyl, and isohexyl groups. Preferred of them are those containing from 1 to 4 carbon atoms, e.g., methyl, ethyl, n-propyl, n-butyl and t-butyl groups.

The terminology "4-lower alkylpiperazinyl group" as used herein means a piperazinyl group substituted by the lower alkyl group, and includes, among others, 4-methylpiperazinyl, 4-ethylpiperazinyl,4-propylpiperazinyl and4-t-butylpiperazinyl groups. Of these, 4-methylpiperazinyl group is the most preferable.

Referring to compounds of the general formula (I) and those of the general formula (II), preferred examples of the substituent -CON($R^2$)$R^3$ on the piperidine ring include carbamoyl, methylcarbamoyl, ethylcarbamoyl, isopropylcarbamoyl, dimethylcarbamoyl, diethylcarbamoyl, 1-aziridinylcarbonyl, 1-azetidinylcarbonyl, 1-pyrrolidinylcarbonyl, piperidinocarbonyl, 1- piperazinylcarbonyl, 4-methyl-1-piperazinylcarbonyl, morpholinocarbonyl and thiomorpholinocarbonyl groups. Particularly preferred are carbamoyl, methylcarbamoyl, dimethylcarbamoyl, 1-pyrrolidinylcarbonyl and piperidinocarbonyl groups.

A represents a single bond, a lower alkylene group, a lower alkenylene group or a lower alkynylene group. Particularly preferred are a single bond and a lower alkenylene group.

The lower alkylene is a straight-chain or branched alkylene group containing from 1 to 4 carbon atoms, such as methylene, ethylene, propylene, tetramethylene, methylmethylene, dimethylmethylene and so on.

The lower alkenylene is an alkenylene group of from 2 to 4 carbon atoms, such as vinylene, propenylene, butenylene, 3-methylpropenylene and so on.

The lower alkynylene means an alkynylene group of from 2 to 4 carbon atoms, such as ethynylene, propynylene, butynylene and so on.

Among compounds of the general formula (I), the preferred are compounds which can be represented by the general formula (I-a):

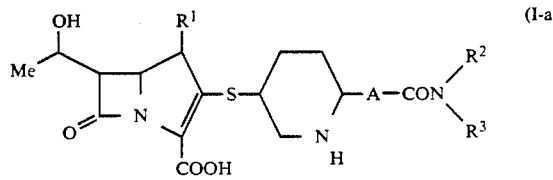

(I-a)

or the general formula (I-b):

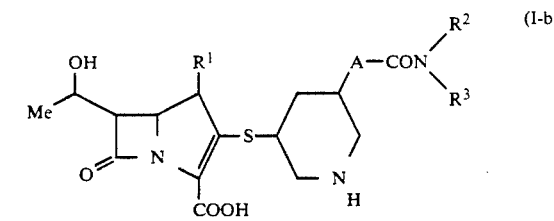

(I-b)

wherein $R^1$, $R^2$, $R^3$ and A are as defined above. Particularly preferred are compounds which can be represented by the general formula (I-a).

The compounds of the general formula (I) further include steric isomers ascribed to asymmetric carbon atoms at the 1-, 5-, 6-, and 8-positions of the carbapenem skeleton.

Of these isomers, preferred are those compounds having a (5R,6S)-configuration similar to the structure of thienamycin and also having the 8-positioned carbon atom in an R-configuration, i.e., those having a (5R,6S,8R)-configuration and, where the 1-position is substituted with a methyl group, those having a (1R,5S,6S,8R)-configuration.

The compounds of the general formula (I) also embrace steric isomers ascribed to asymmetric carbon atoms on the piperidylthio group at the 2-position of the carbapenem skeleton.

Among compounds of the general formula (I), the preferred are compounds, having a preferred configuration, which can be represented by the general formula (I₁):

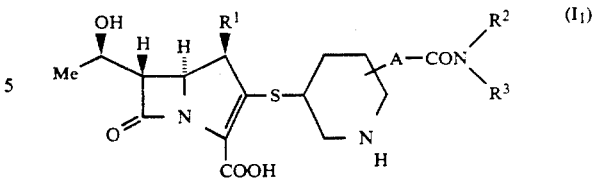

(I₁)

wherein $R^1$, $R^2$, $R^3$ and A are as defined above.

Among compounds of the general formula (I₁), the more preferred are compounds, having a preferred configuration, which can be represented by the general formula (I₁-a):

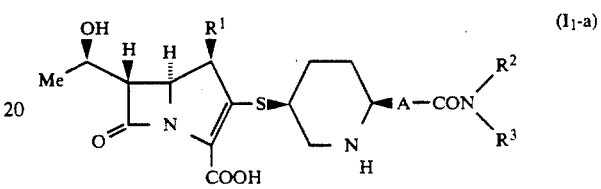

(I₁-a)

or the general formula (I₁-b):

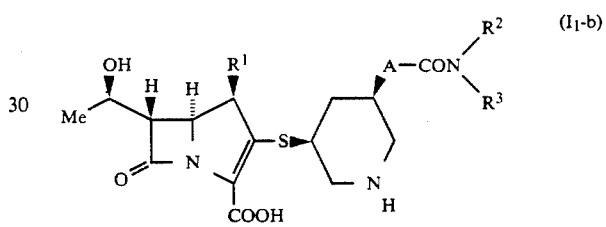

(I₁-b)

wherein $R^1$, $R^2$, $R^3$ and A are as defined above. Particularly preferred are compounds which can be represented by the general formula (I₁-a).

Specific examples of the compounds of the general formula (I) are shown below.

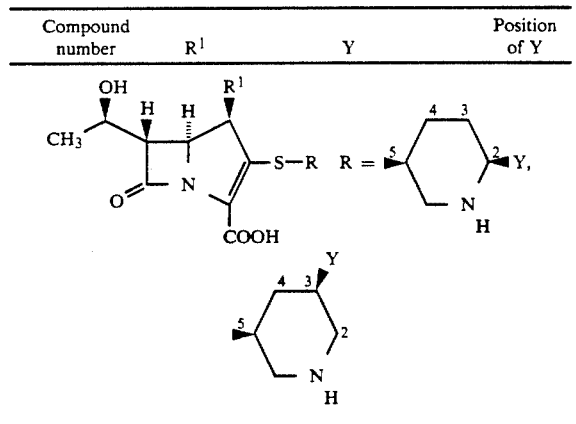

| Compound number | $R^1$ | Y | Position of Y |
|---|---|---|---|
| 1 | H | $CONH_2$ | 2 |
| 2 | H | $CONHCH_3$ | 2 |
| 3 | H | $CONHC_2H_5$ | 2 |
| 4 | H | $CONH(n-C_3H_7)$ | 2 |
| 5 | H | $CONH(iso-C_3H_7)$ | 2 |
| 6 | H | $CONH(n-C_4H_9)$ | 2 |
| 7 | H | $CONH(tert-C_4H_9)$ | 2 |
| 8 | H | $CON(CH_3)_2$ | 2 |
| 9 | H | $CON(C_2H_5)_2$ | 2 |
| 10 | H | $CON(iso-C_3H_7)_2$ | 2 |
| 11 | H | $CON(CH_3)C_2H_5$ | 2 |

-continued

| Compound number | R¹ | Y | Position of Y |
|---|---|---|---|
| 12 | H | CON⟨azetidinyl (3-membered N-ring)⟩ | 2 |
| 13 | H | CON⟨azetidinyl (4-membered)⟩ | 2 |
| 14 | H | CON⟨pyrrolidinyl⟩ | 2 |
| 15 | H | CON⟨piperidinyl⟩ | 2 |
| 16 | H | CON⟨piperazinyl-NH⟩ | 2 |
| 17 | H | CON⟨N-methylpiperazinyl⟩ | 2 |
| 18 | H | CON⟨morpholinyl (O)⟩ | 2 |
| 19 | H | CON⟨thiomorpholinyl (S)⟩ | 2 |
| 20 | $CH_3$ | $CONH_2$ | 2 |
| 21 | $CH_3$ | $CONHCH_3$ | 2 |
| 22 | $CH_3$ | $CONHC_2H_5$ | 2 |
| 23 | $CH_3$ | $CONH(n\text{-}C_3H_7)$ | 2 |
| 24 | $CH_3$ | $CONH(\text{iso-}C_3H_7)$ | 2 |
| 25 | $CH_3$ | $CONH(n\text{-}C_4H_9)$ | 2 |
| 26 | $CH_3$ | $CONH(\text{tert-}C_4H_9)$ | 2 |
| 27 | $CH_3$ | $CON(CH_3)_2$ | 2 |
| 28 | $CH_3$ | $CON(C_2H_5)_2$ | 2 |
| 29 | $CH_3$ | $CON(\text{iso-}C_3H_7)_2$ | 2 |
| 30 | $CH_3$ | $CON(CH_3)C_2H_5$ | 2 |
| 31 | $CH_3$ | CON⟨aziridinyl⟩ | 2 |
| 32 | $CH_3$ | CON⟨azetidinyl⟩ | 2 |
| 33 | $CH_3$ | CON⟨pyrrolidinyl⟩ | 2 |
| 34 | $CH_3$ | CON⟨piperidinyl⟩ | 2 |
| 35 | $CH_3$ | CON⟨piperazinyl-NH⟩ | 2 |
| 36 | $CH_3$ | CON⟨N-methylpiperazinyl⟩ | 2 |
| 37 | $CH_3$ | CON⟨morpholinyl (O)⟩ | 2 |
| 38 | $CH_3$ | CON⟨thiomorpholinyl (S)⟩ | 2 |
| 39 | H | $CONH_2$ | 3 |
| 40 | H | $CONHC_2H_5$ | 3 |
| 41 | H | $CONH(n\text{-}C_4H_9)$ | 3 |
| 42 | H | $CON(C_2H_5)_2$ | 3 |
| 43 | H | CON⟨aziridinyl⟩ | 3 |
| 44 | H | CON⟨piperidinyl⟩ | 3 |
| 45 | H | CON⟨morpholinyl (O)⟩ | 3 |
| 46 | $CH_3$ | $CONHCH_3$ | 3 |
| 47 | $CH_3$ | $CONH(\text{iso-}C_3H_7)$ | 3 |
| 48 | $CH_3$ | $CON(CH_3)_2$ | 3 |
| 49 | $CH_3$ | $CON(CH_3)C_2H_5$ | 3 |
| 50 | $CH_3$ | CON⟨piperidinyl⟩ | 3 |
| 51 | $CH_3$ | CON⟨N-methylpiperazinyl⟩ | 3 |
| 52 | $CH_3$ | $CH=CH-CONH_2$ | 2 |
| 53 | H | $CH=CH-CONH_2$ | 2 |
| 54 | $CH_3$ | $C\equiv C-CONH_2$ | 2 |

Structure:

Carbapenem core with OH-CH(CH₃)- at C6, R¹ at C5, S–R at C2, COOH at C3; R = piperidinyl substituted with Y at position 4, attached at position 3 to S, with NH at position 2.

| Compound number | R¹ | Y | Position of Y |
|---|---|---|---|
| | | ![piperidine structure with positions 2,3,4 and N-H, Y at position 2] | |
| 55 | H | CONHCH₃ | 4 |
| 56 | H | CONH(n-C₃H₇) | 4 |
| 57 | H | CONH(iso-C₃H₇) | 2 |
| 58 | H | CONH(tert-C₄H₉) | 4 |
| 59 | H | CON(CH₃)₂ | 2 |
| 60 | H | CON(iso-C₃H₇)₂ | 4 |
| 61 | H | CON(CH₃)C₂H₅ | 2 |
| 62 | H | CON⟨azetidine⟩ | 4 |
| 63 | H | CON⟨pyrrolidine⟩ | 2 |
| 64 | H | CON⟨piperazine⟩NH | 4 |
| 65 | H | CON⟨piperazine⟩N—CH₃ | 2 |
| 66 | H | CON⟨thiomorpholine⟩S | 4 |
| 67 | CH₃ | CONH₂ | 2 |
| 68 | CH₃ | CONHC₂H₅ | 4 |
| 69 | CH₃ | CONH(n-C₃H₇) | 2 |
| 70 | CH₃ | CONH(n-C₄H₉) | 4 |
| 71 | CH₃ | CONH(tert-C₄H₉) | 2 |
| 72 | CH₃ | CON(C₂H₅)₂ | 2 |
| 73 | CH₃ | CON(iso-C₃H₇)₂ | 2 |
| 74 | CH₃ | CON⟨azetidine⟩ | 4 |
| 75 | CH₃ | CON⟨azetidine⟩ | 2 |
| 76 | CH₃ | CON⟨piperidine⟩ | 4 |
| 77 | CH₃ | CON⟨piperazine⟩NH | 2 |
| 78 | CH₃ | CON⟨morpholine⟩O | 4 |
| 79 | CH₃ | CON⟨thiomorpholine⟩S | 2 |

The preferred examples of the compound listed above are as follows:

(1) (5R,6S)-2-[(2S,5S)-2-carbamoylpiperidin-5-yl]thio-6-[(1R)-1-hydroxyethyl]-1-carbapen-2-em-3-carboxylic acid (2) (5R,6S)-6-[(1R)-1-hydroxyethyl]-2-[(2S,5S)-2-methylcarbamoylpiperidin-5-yl]thio-1-carbapen-2-em-3-carboxylic acid (3) (5R,6S)-2-[(2S,5S)-2-ethylcarbamoylpiperidin-5-yl]thio-6[(1R)-1-hydroxyethyl]-1-carbapen-2-em-3-carboxylic acid (8) (5R,6S)-2-[(2S,5S)-2-dimethylcarbamoylpiperidin-5-yl]thio6-[(1R)-1-hydroxyethyl]-1-carbapen-2-em-3-carboxylic acid

(11) (5R,6S)-2-[(2S,5S)-2-ethylmethylcarbamoylpiperidin-5-yl]-thio-6-[(1R)-1-hydroxyethyl]-1-carbapen-2-em-3-carboxylic acid

(14) (5R,6S)-6-[(1R)-1-hydroxyethyl]-2-[(2S,5S)-2-(1-pyrrolidinyl)carbonylpiperidin-5-yl]thio-1-carbapen-2-em-3-carboxylic acid

(16) (5R,6S)-6-[(1R)-1-hydroxyethyl]-2-[(2S,5S)-2-(1-piperazinyl) carbonyl acid

(20) (1R,5S,6S)-2-[(2S,5S)-2-carbamoylpiperidin-5-yl]thio-6[(1R)-1-hydroxyethyl]-1-methylcarbapen-2-em-3-carboxylic acid

(21) (1R,5S,6S)-6-[(1R)-1-hydroxyethyl]-2-[(2S,5S)-2-methylcarbamoylpiperidin-5-yl]thio-1-methylcarbapen2-em-3-carboxylic acid

(22) (1R,5S,6S)-2-[(2S,5S)-2-ethylcarbamoylpiperidin-5-yl]thio6-[(1R)-1-hydroxyethyl]-1-methylcarbapen-2-em-3-carboxylic acid

(27) (1R,5S,6S)-2-[(2S,5S)-2-dimethylcarbamoylpiperidin-5yl]thio-6-[(1R)-1-hydroxyethyl]-1-methylcarbapen-2-em-3carboxylic acid

(30) (1R,5S,6S)-2-[(2S,5S)-2-ethylmethylcarbamoylpiperidin-5yl]thio-6-[(1R)-1-hydroxyethyl]-1-methylcarbapen-2-em-3carboxylic acid

(33) (1R,5S,6S)-6-[(1R)-1-hydroxyethyl]-2-[(2S,5S)-2-(1-pyrrolidinyl) carbonylpiperidin-5-yl]thio-1-methylcarbapen-2-em-3-carboxylic acid

(35) (1R,5S,6S)-6-[(1R)-1-hydroxyethyl]-2-[(2S,5S)-2-(1-piperazinyl)carbonylpiperidin-5-yl]thio-1-methylcarbapen -2-em-3-carboxylic acid

(39) (5R,6S)-2-[(3S,5S)-3-carbamoylpiperidin-5-yl]thio-6-[(1R) 1-hydroxyethyl]-1-carbapen-2-em-3-carboxylic acid

(40) (5R,6S)-2-[(3S,5S)-3-ethylcarbamoylpiperidin-5-yl]thio-6-[(1R)-1-hydroxyethyl]-1-carbapen-2-em-3-carboxylic acid

(46) (1R,5S,6S)-6-[(1R)-1-hydroxyethyl]-2-[(3S,5S)-3-methylcarbamoylpiper-5-yl]thio-1-methylcarbapen-2-em-3-carboxylic acid

(48) (1R,5S,6S)-2-[(3S,5S)-3-dimethylcarbamoylpiperidin-5- yl]thio-6-[(1R)-1-hydroxyethyl]-1-methylcarbapen-2-em-3carboxylic acid

(50) (1R,5S,6S)-6-[(1R)-1-hydroxyethyl]-2-[(3S,5S)-3-(1-pyrrolidinyl) carbonylpiperidin-5-yl]thio-1-methylcarbapen-2-em-3-carboxylic acid

(52) (1R,5S,6S)-2-[(2R,5S)-2-carbamoylvinylpiperidin-5-yl]thio6-[(1R)-1-hydroxyethyl]-1-methylcarbapen-2-em-3-carboxylic acid

(53) (5R,6S)-2-[(2R,5S)-2-carbamoylvinylpiperidin-5-yl]thio-6[(1R)-1-hydroxyethyl]-1-carbapen-2-em-3-carboxylic acid

(55) (5R,6S)-6-[(1R)-1-hydroxyethyl]-2-[(3S,4R)-4-methyl -carbamoylpiperidin-3-yl]-2-em-3-carboxylic acid

(56) (5R,6S)-6-[(1R)-1-hydroxyethyl]-2-[(3S,4R) -4-n-propyl-carbamoylpiperidin-3-yl]thio-1-carbapen-2-em-3-carboxylic acid

(59) (5R,6S)-2-[(2S,3S)-2-dimethylcarbamoylpiperidin-3-yl]thio6-[(1R)-1-hydroxyethyl]-1-carbapen-2-em-3-carboxylic acid

(67) (1R,5S,6S)-2-[(2S,3S)-2-carbamoylpiperidin-3-yl]thio-6[(1R)-1-hydroxyethyl]-1-methylcarbapen-2-em-3-carboxylic acid and

(68) (1R,5S,6S)-2-[(3S,4R)-4-ethylcarbamoylpiperidin-3-yl]thio6-[(1R)-1-hydroxyethyl]-1-methylcarbapen-2-em-3-carboxylic acid.

Especially the compounds of (1), (2), (8), (20), (21), (27), (52) and (53) are preferred, and the most preferable compound is (27) among the above compounds.

The compounds of the general formula (I) can be converted to pharmaceutically acceptable non-toxic salts or esters thereof in a usual manner.

The non-toxic salts of the compound (I) may be any of the pharmaceutically acceptable salts which are commonly employed in the art and mean salts formed at the carboxyl group at the 3-position of the carbapenem skeleton or on the nitrogen atom on the piperidine ring at the 2-position of the carbapenem skeleton. Examples of such salts include salts with alkali metals (e.g. sodium, potassium, lithium, etc.), salts with alkaline earth metals (e.g. calcium, magnesium, etc.), salts with organic amines (e.g. N,N'-dibenzylethylenediamine, ethanolamine, triethylamine, etc.), salts with inorganic acids (e.g. hydrochloric acid, nitric acid, sulfuric acid, phosphoric acid, etc.), salts with organic acids (e.g. citric acid, tartaric acid, etc.), salts with organic sulfonic acids (e.g. methanesulfonic acid, p-toluenesulfonic acid, etc.) and salts with amino acids (e.g. aspartic acid, glutamic acid, lysine, etc.).

The non-toxic esters of the compounds of the general formula (I) may be any of the pharmaceutically acceptable and commonly employed esters which are formed at the carboxyl group at the 3-position of the carbapenem skeleton. Examples of such esters include esters with an alkanoyloxymethyl group (e.g., acetoxymethyl, pivaloyloxymethyl, etc.), esters with an alkoxycarbonyloxyalkyl group (e.g., 1-(ethoxycarbonyloxy)ethyl etc.), esters with a phthalidyl group and esters with 5-substituted2-oxo-1,3-dioxol-4-ylmethyl group (e.g., 5-methyl-2-oxo-1,3-dioxol-4-ylmethyl, etc.).

The process for producing compounds (I) of the invention is described below.

The compound of the general formula (I) can be produced by reacting a compound represented by the general formula (III):

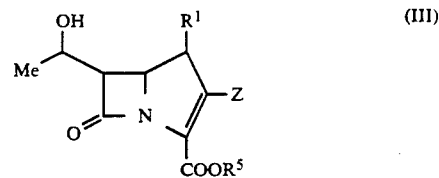

wherein $R^1$ is a hydrogen atom or a methyl group; $R^5$ is a carboxyl-protective group; and Z is a leaving group, with a compound represented by the general formula (II):

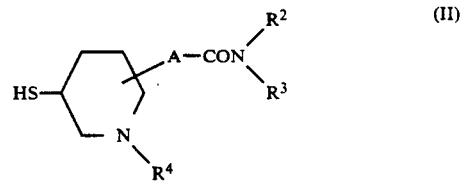

wherein $R^2$ and $R^3$, which may be the same or different, each represents a hydrogen atom or a lower alkyl group, or taken together with the adjacent nitrogen atom, jointly represent a heterocyclic group selected from the group consisting of an aziridinyl group, an azetidinyl group, a pyrrolidinyl group, a piperidino group, a piperazinyl group, a 4-lower alkylpiperazinyl group, a morpholino group and a thiomorpholino group; $R^4$ is a hydrogen atom or an imino-protective group; and A is a single bond, a lower alkylene group, a lower alkenylene group or a lower alkynylene group, and removing the protective group or groups.

The reaction between the compound (II) and the compound (III) can be carried out in the presence of a base (e.g., N,N-diisopropylethylamine, triethylamine, 4-dimethylaminopyridine, etc.) in an inert solvent which does not adversely affect the reaction (e.g., acetonitrile, N,N-dimethylformamide (hereinafter abbreviated as DMF), dimethylacetamide, N-ethylpyrrolidinone, etc.) at a temperature between -40° C. and 25° C. for from 5 minutes to 10 hours. The starting compounds are used in substantially equimolar compounds and the base is used in a proportion of from 1 to 2 equivalents.

The leaving group represented by Z in the general formula (III) means an acyl group derived from an organic phosphoric acid or organic sulfonic acid. Examples of suitable leaving groups include diphenoxylphosphoryloxy, methanesulfonyloxy, trifluoromethanesulfonyloxy, p-toluenesulfonyloxy and so on. Particularly preferred are diphenoxylphosphoryloxy and methanesulfonyloxy.

The imino-protective group in the general formula (II) and the carboxyl-protective group in the general formula (III) may be the corresponding groups commonly used in the art. These protective groups can be eliminated by the per se known deprotection reactions suited to the particular species to give the desired compound (I).

In typical examples, when the imino-protective group is a p-nitrobenzyloxycarbonyl group, and the carboxyl-protective group is a p-nitrobenzyl group, these protective groups can be eliminated by treating the reaction product in a mixed solvent (e.g., tetrahydrofuran (hereinafter abbreviated as THF)-water, dioxane-ethanol-water, butanol-water, etc.) containing a phosphoric acid buffer, a 3-morpholinopropanesulfonic acid buffer, dipotassium phosphate, etc. (pH=7) in the presence of a catalyst for hydrogenation, e.g., palladium-on-activated carbon, palladium hydroxide and platinum oxide, at a hydrogen pressure of from 1 to 4 atm. and at a temperature of from 0° to 50° C. for a period of from 20 minutes to 4 hours. When the imino-protective group is an allyloxycarbonyl group, and the carboxyl-protective group is an allyl group, these protective groups can be eliminated by treating the reaction product in an inert solvent (e.g., THF, diethyl ether, dichloromethane, etc.) in the presence of a catalyst comprising a palladium compound and triphenylphosphine.

The compound of formula (III) may be produced from bicyclic keto esters according to, for example, the process disclosed in T.N. Salzmann et al., *J. Am. Chem. Soc.*, Vol. 102, p. 6161 (1980) or D.H. Shih et al., *Heterocvcles*, Vol. 21, p. 29 (1984) or analogues thereof. The compound thus obtained may be used for the reaction with the compound of formula (II) without being isolated from the reaction mixture.

The compounds (II) which can be used with advantage as the side chain moiety of the compound (I) and the processes for production of these compounds (II) are described below.

The compound of the general formula (II) is an unreported novel compound, serving as an important intermediate for the production of the compound (I).

The present invention is, therefore, directed also to a compound represented by the general formula (II) as defined above, and a process for producing the same.

Among compounds of the general formula (II), preferred are those represented by the general formula (II-a):

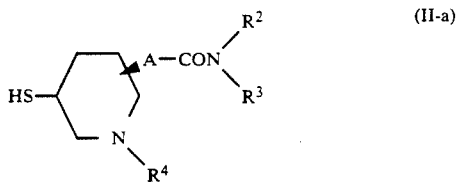

wherein $R^2$, $R^3$, $R^4$ and A are as defined above.

More preferred are the compounds in which the substituent

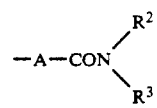

is situated alpha to the nitrogen atom.

The compound of the general formula (II) can be produced, for example, by the following steps.

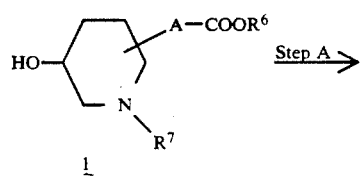

-continued

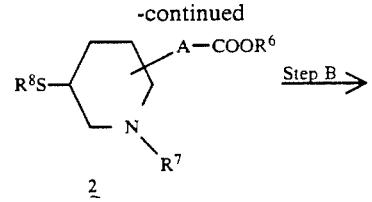

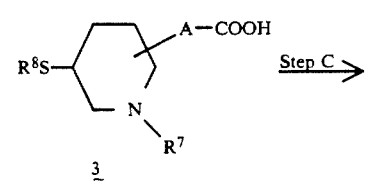

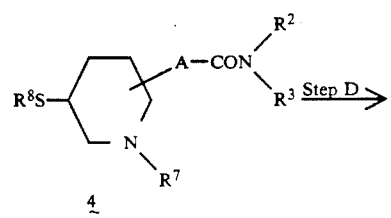

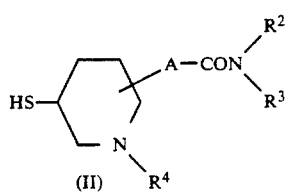

In the above formulas, $R^2$, $R^3$, $R^4$ and A are respectively as defined above; $R^6$ is a carboxyl-protective group; $R^7$ is an imino-protective group; and $R^8$ is a mercapto-protective group.

Step A

In this step, the hydroxyl group of compound 1, which is either a known compound (B. Witkop et al., *J. Am. Chem. Soc.*, Vol. 79, p. 192 (1957) or a compound which can be synthesized by a process analogous to any of the processes described in the literature (e.g., P.D. Baiky et al., *Tetrahedron Letters*, Vol. 29, p. 2231 (1988), etc.), is converted to a protected mercapto group.

Step A can be carried out by various known techniques for converting a hydroxyl group to a protected mercapto group. For example, the hydroxyl group of compound 1 is converted to an active ester form (e.g., a mesyloxy group, a tosyloxy group, etc.) or a halogen atom (e.g., chlorine, bromine, iodine, etc.), and the resulting active ester derivative or halogeno derivative is then reacted with a reagent for substituting oxygen with sulfur (e.g., thioacetic acid, thiobenzoic acid, tritylmercaptan, p-methoxybenzylmercaptan, etc.) (hereinafter referred to as thio-reagent) in the presence of a base (e.g., triethylamine, diisopropylethylamine, N-methylmorpholine, 1,8-diazabicyclo[5.4.0]-7-undecene (hereinafter abbreviated as DBU), sodium hydroxide, potassium t-butoxide, sodium methoxide, sodium hydride, etc.).

Amounts of reagents to be used are appropriately selected depending on the reaction conditions and the like. Generally, the thio-reagent is used in an amount of from 1 to 5 mols, preferably from 1 to 2 mols, per mol of compound 1, and the base is used in an amount of from 1 to 5 mols, preferably from 1 to 2 mols, per mol of compound 1. The reaction can be carried out in an inert solvent which does not adversely affect the reaction (e.g., dichloromethane, THF, DMF, etc.) or a mixture thereof. The reaction temperature usually ranges from −60° to 80° C., and preferably from −20° to room temperature. The reaction time is usually from 15 minutes to 16 hours, and preferably from 30 minutes to 2 hours.

Step A may also be effected by reacting compound 1 with the thio-reagent (e.g., thioacetic acid, etc.) in an inert solvent (e.g., THF, etc.), in the presence of triphenylphosphine and diethyl azodicarboxylate. The amount each of triphenylphosphine, diethyl azodicarboxylate and the thioreagent to be used suitably ranges from 1 to 5 mols, preferably from 1 to 2 mols, per mol of compound 1, though somewhat varying depending on the reaction conditions and the like. The reaction is usually conducted at a temperature of from 0° to 70° C. for a period of from 15 minutes to 24 hours.

Step B

In this step, the carboxyl-protective group of compound 2 is eliminated.

Step B can be achieved by a process selected according to the kind of the ester residue $COOR^6$ from among various known techniques for converting an ester group to a carboxyl group, for example, alkali hydrolysis, treatment with an acid (e.g., trifluoroacetic acid, hydrobromic acid, etc.), catalytic reduction and a reductive process using zinc, etc.

Step C

In this step, the carboxyl group of compound 3 is converted to a substituted or unsubstituted carbamoyl group.

Step C can be implemented by various known processes for conversion of a carboxyl group to a carbamoyl group, for example converting the carboxyl group to a reactive derivative such as acid chloride, acid anhydride and active ester, and then reacting this reactive derivative with an optional kind of amine compound. In an alternative process, compound 3 is reacted with such an amine compound in the presence of a condensing agent such as N,N'-dicyclohexylcarbodiimide (hereinafter abbreviated as DCC), silicon tetrachloride and the like.

The amount of the amine compound is dependent on conditions of reaction and other factors, but generally from 1 to 5 moles of the amine compound is advantageously used relative to each mole of compound 3. The reaction can be conducted at a temperature of from −20° C. to 80° C. and goes to completion for a period of from 1 to 24 hours.

Step D

In this step, the mercapto-protective group of compound 4 is eliminated.

Step D can be achieved by various known techniques for elimination of a protective group of a mercapto group. For example, alkali hydrolysis is employed for removal of an acyl group, and a hydrolysis with an acid such as trifluoroacetic acid, trifluoromethanesulfonic acid, etc. is employed for elimination of a trityl group, a p-methoxybenzyl group, etc.

The thus prepared compound of the general formula (II) may be reacted with the compound of the general formula (III) without being isolated from the reaction mixture.

The compound of the general formula (II) may occur as stereoisomers due to the asymmetric carbon atoms on the piperidine ring and all of these isomers fall within the scope of the invention. Such isomers can be obtained by the above procedure using the starting compounds having the specific configurations, if necessary in combination with the known steric inversion reaction.

The compounds of the general formula (I) according to the present invention are new and exhibit excellent antibacterial activity and are useful as drugs for treating and preventing bacterial infectious diseases, such as respiratory infectious diseases, urinary infectious diseases, suppurative diseases and surgical infectious diseases.

The compound of the general formula (I) are nonorally administered by, for example, intravenous injection, intramuscular injection or as suppositories, etc., or orally administered in the form of tablets, powders, capsules, syrups, etc. The compound of the general formula (I) can be formulated into these dosage forms by various known methods. For example, the compound is mixed with generally employed additives, such as adjuvants, wetting agents, emulsifying agents, binders, vehicles and the like. The dose of the compound is decided depending on the age, sex, body weight, and difference in susceptibility of a patient, the route, time, and interval of administration, the degree of symptoms, the physical condition of a patient, the properties, kind, and active ingredients of the preparation and the like. In general, the compound is preferably administered at a dose ranging from 1 to 100 mg/kg per day in from 2 to 4 divided doses (5 to 30 mg/kg/dose).

The in vitro antibacterial activity of the compound of the present invention was determined according to an agar plate dilution method as follows. A test microorganism was cultured in a Mueller-Hinton's medium overnight, and a loopful of the microbial cells was inoculated to a Mueller-Hinton-agar medium ($10^6$ CFU/ml) containing the test compound in a prescribed concentration and cultured at 37° C. for 16 hours to obtain a minimum growth inhibition concentration (MIC: μg/ml). As a result, MIC of the compound of Example 1 hereinafter described against *E. coli* NIHJ JC-2 was 0.025 μg/ml.

The present invention is now illustrated in greater detail by way of Examples, but it should be understood that the present invention is not deemed to be limited thereto. Abbreviations used herein have the following meanings.

Me : methyl
Et : ethyl
Cbz : benzyloxycarbonyl
Alloc : allyloxycarbonyl
PNZ : p-nitrobenzyloxycarbonyl
PMB : p-methoxybenzyl
Ac : acetyl
Ph : phenyl
PNB : p-nitrobenzyl
Ms : methanesulfonyl
Tr : trityl

EXAMPLE 1

(1R,5S,6S)-2-[(2S,5S)-2-Dimethylcarbamoylpiperidin-5-yl]thio-(1S)-1-hydroxyethyl]-1-methylcarbapen-2-em-3-carboxylic Acid

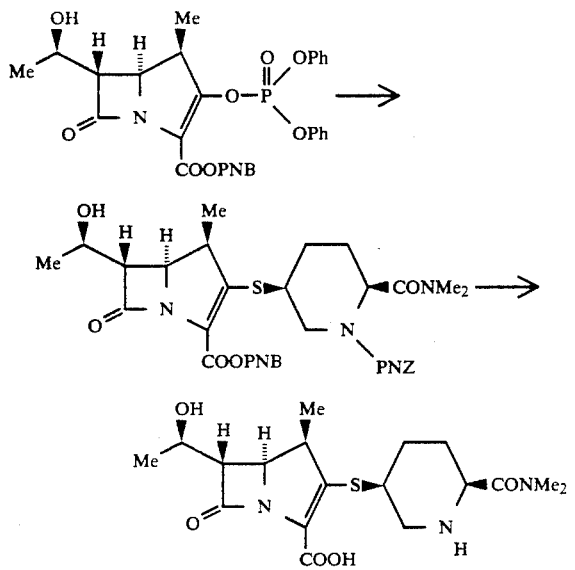

a) Under a nitrogen atmosphere, 1.12 g (1.88 mmol) of p-nitrobenzyl (1R,5S,6S)-2-diphenylphosphoryloxy-6-[(1R)-1-hydroxyethyl]-1-methylcarbapen-2-em-3-carboxylate was dissolved in 30 ml of acetonitrile. To this solution was added 0.38 ml (2.18 mmol) of diisopropylethylamine followed by a dropwise addition of a solution of the compound prepared in Example 8 in acetonitrile (10 ml) under ice-cooling. The solution was stirred for 1 hour under ice-cooling, and then for 4 hours at room temperature. The resulting solution was left overnight at $-20°$ C., and again stirred for 3 hours at room temperature. To the reaction mixture was added 160 ml of ethyl acetate, the organic layer was washed with 40 ml of water followed by saturated aqueous sodium chloride. After the extract was dried over anhydrous sodium sulfate, the solvent was removed. The residue was purified by silica gel column chromatography (Wakogel ® C-300, elution with ethyl acetate - dichloromethane system) to give 1.07 g (yield: 84%) of p-nitrobenzyl (1R,5S,6S)-2-[(2S,5S)-2-dimethylcarbamoyl -1-p-nitrobenzyloxy -carbonylpiperidin-5-yl]thio-6-[(1R)-1-hydroxyethyl]-1-methylcarbapen-2-em-3-carboxylate.

IR (KBr) cm$^{-1}$: 3450, 1770, 1700, 1640, 1520, 1340
NMR (CDCl$_3$) δ: 1.22 (3H,d,J=7Hz), 1.32 (3H,d,J=7Hz),
1.70-2.20 (4H,m), 2.95 (3H,s), 3.06 (3H,s),
3.10-3.40 (2H,m), 3.40-3.70 (2H,m), 3.90
4.40 (4H,m), 4.90-5.10 (1 H,m), 5.18 and
5.32 (2H,ABq,J=14Hz), 5.24-5.50 (2H,ABq, J=14Hz), 7.47 and 7.53 (2H, each d, J=8Hz),
7.66 (2H,d,J=8Hz), 8.24 (2H,d,J=8Hz), 8.28 (2H,d,J=8Hz)

b) A suspension of 1.3 g of 10% palladium-carbon in 10 ml of 0.1 M 3-morpholinopropanesulfonate buffer (pH 7.0) was stirred for 1 hour under a hydrogen atmosphere, and the catalyst was collected by filtration and washed with water. This catalyst was added to a solution of 1.07 g (1.5 mmol) of the compound prepared in the above reaction a) in THF (80 ml)—ethanol (12 ml)—0.1 M 3-morpholinopropanesulfonate buffer (pH 7.0, 80 ml), and the mixture was hydrogenated at atmospheric pressure and room temperature for 2 hours. The catalyst was removed by filtration, and the filtrate was concentrated in order to remove THF and ethanol in vacuo. The residual aqueous solution was washed with 100 ml of ethyl acetate, and a small amount of insoluble matter was removed by filtration.

The resulting aqueous solution was again concentrated in vacuo, and then purified by reversed phase column chromatography (Chemco LC-SORB ®, SP-B-ODS, elution with 0-25% methanol—water), and lyophilized to give 395 mg (yield: 60%) of the title compound.

IR (KBr) cm$^{-1}$: 3400, 1750, 1620, 1400
UV $\lambda_{max}$ (0.1 M 3-morpholinopropanesulfonate buffer, pH 70): 297 nm (ε=8 600)
NMR (D$_2$O) δ: 1.17 (3H,d,J=7Hz), 1.26 (3H,d,J=7Hz),
1.70-2.40 (4H,m), 2.94 (3H,s), 3.06 (3H,s),
3.20-3.60 (3H,m), 3.60-3.70 (1H,m), 4.10-4.40 (3H,m)

EXAMPLE 2

(5R,6S)-2-(2S,5S)-2-Dimethylcarbamoylpiperidin-5-yl]thio-6-[(1R)-1-hydroxyethyl]-1-carbapen-2-em-3-carboxylic Acid

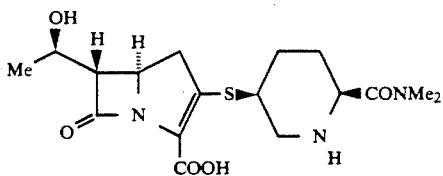

Thirty-one mg of the title compound was obtained from (2S,5S)-2-dimethylcarbamoyl-5-mercapto-1-p-nitrobenzyloxycarbonylpiperidine and 183 mg of p-nitrobenzyl-(5R,6S)-6-[(1R)-1-hydroxyethyl]-2-diphenylphosphoryloxy-1-carbapen-2-em-3-carboxylate in the same manner as in Example 1.

IR (KBr) cm$^{-1}$: 3400, 1760, 1620, 1390
NMR (D$_2$O) δ: 1.22 (3H,d,J=7Hz), 1.60-2.40 (4H,m), 2.90 (3H,s), 3.03 (3H,s), 3.00-3.45 (4H,m),
3.55-3.75 (1 H,m), 4.05-4.30 (3H,m)

EXAMPLE 3

(1R,5S,6S)-2-(2S,5S)-2-Carbamoylpiperidin-5-yl]thio-6-[(1R)-1-hydroxyethyl]-1-methylcarbapen-2-em-3-carboxylic Acid

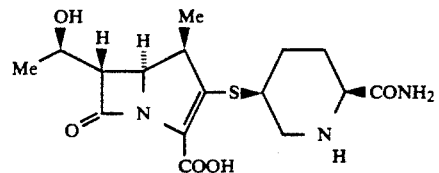

Three hundred and twenty-one mg of the title compound was obtained from (2S,5S)-2-carbamoyl-5-mercapto-1-p-nitrobenzyloxycarbonylpiperidine and 1.2 g of p-nitrobenzyl (1R,5S,6S)-2-diphenylphosphoryloxy-6-[(1R)-1-hydroxyethyl]-1-methylcarbapen -2-em-3-carboxylate in the same manner as in Example 1.

IR (KBr) cm$^{-1}$: 3420, 2960, 1755, 1690, 1620, 1390
UV $\lambda_{max}$ (0.1 M 3-morpholinopropanesulfonate buffer, pH 7.0): 299 nm (ε=8,100)
NMR (D$_2$O) δ: 1.17 (3H,d,J=7Hz), 1.26 (3H,d 1.80-2.40 (4H,m), 2.90-3.10 (1 H,m), 3.10-3.50 (3H,m), 3.50-3.70 (1 H,m), 3.70-4.00 (1 H,m), 4.10-4.40 (2 H,m)

EXAMPLE 4

(5R,6S)-2-[(2S,5S)-2-Carbamoylpiperidin-5-vl]thio-6-[(1R)-1hydroxyethyl]-1-carbapen-2em-3-carboxylic Acid

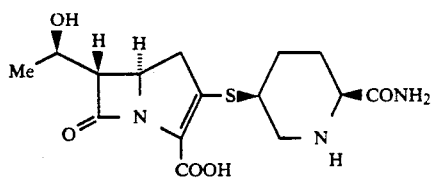

Eight mg of the title compound was obtained from (2S,5S)-2-carbamoyl-5-mercapto-1-nitrobenzyloxycarbonylpiperidine and 140 mg of P-nitrobenzyl (5R,6S)-2-diphenyl-phosphoryloxy-6-[(1R)-1-hydroxyethyl]-1-carbapen-2-em-3rboxylate in the same manner as in Example 1.

IR (KBr) cm$^{-1}$: 3400, 1760, 1690, 1590, 1390

UV $\lambda_{max}$ (0.1 M 3-morpholinopropanesulfonate buffer, pH 7.0): 299 nm ($\epsilon$=7,700)

EXAMPLE 5

(1R,5S,6S)-6-[(1R)-1-Hydroxyethyl]-2-[(2S,5S)-2-methyl-carbamoylpiperidin-5-vl]thio-1-methylcarbapen-2-em-3-carboxylic Acid

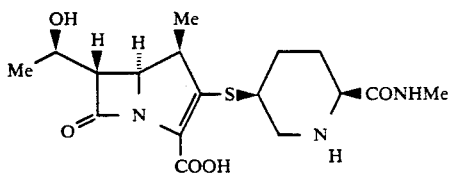

Ten mg of the title compound was obtained from 250 mg of p-nitrobenzyl (1R,5S,6S)-2-diphenylphosphoryloxy-6-[(1R)-1-hydroxyethyl]-1-methylcarbapen-2-em-3-carboxylate and the compound prepared in Example 9 in the same manner as in Example 1.

IR (KBr) cm$^{-1}$: 3430, 1760, 1680, 1600, 1400, 1180, 1050

UV $\lambda_{max}$ (0.1 M 3-morpholinopropanesulfonate buffer, pH 7.0): 299 nm ($\epsilon$=6,600)

NMR (D$_2$O) $\delta$: 1.14 (3H,d,J=7Hz), 1.23 (3H,d,J=6Hz),
1.80-2.30 (4H,m), 2.72 (3H,s), 2.80-3.10 (1 H,m), 3.10-3.50 (3H,m), 3.50-3.70 (1 H,m), 3.60-3.90 (1 H,m), 4.00-4.20 (2H,m)

EXAMPLE 6

(1R,5S,6S)-2-(2R,5S)-2-(trans-2-Carbamoylvinylpiperidin-5-yl]thio-6-(1R)-1-hydroxyethyl]-1-methylcarbapen-2-em-3-carboxylic Acid

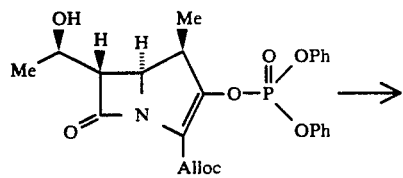

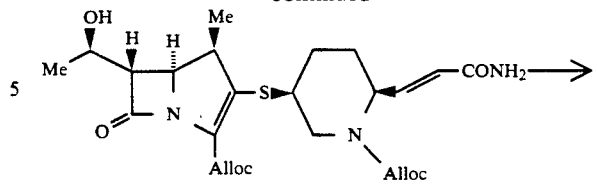

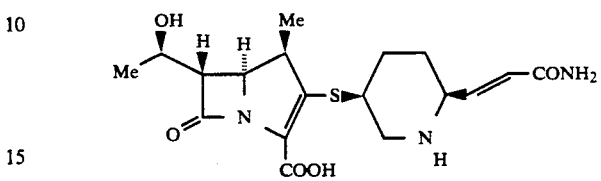

a) Under a nitrogen atmosphere, 130 mg (0.26 mmol) of allyl (1R,5S,6S)-2-diphenylphosphoryloxy-6-[(1R)-1hydroxyethyl]-1-methylcarbapen-2-em-3-carboxylate was dissolved in 2 ml of acetonitrile. To this solution was added 70 mg of the compound prepared in Example 10 followed by a very slow dropwise addition of 0.045 ml (0.258 mmol) of diisopropylethylamine at −40 to −30° C. The mixture was stirred for 5 hours at the same temperature, and then overnight at 5° C. To the mixture was added 30 ml of ethyl acetate, and the organic layer was washed with water, and dried over anhydrous sodium sulfate. The solvent was removed, and the residue was purified by silica gel column chromatography (Wakogel ®  C-300, elution with methanol - chloroform system) to give 60 mg (yield: 45%) of allyl (1R,5S,6S)-2-[(2R,5S)-1-allyloxycarbonyl-2-(2-carbamoylvinyl)-piperidin -5-yl]thio-6-[(1R)-1-hydroxyethyl]-1-methyl-carbapen-2-em-3-carboxylate. IR (KBr) cm$^{-1}$: 3430, 2930, 1770, 1700, 1690, 1645, 1415, 1320, 960

NMR (CDCl$_3$) $\delta$: 1.24 (3H,d,J=7Hz), 1.34 (3H,d,J=7Hz), 1.40-2.20 (4H,m), 2.80-3.20 (3H,m), 3.20-3.30 (1H,m), 3.30-3.60 (2H,m), 3.70-4.60 (2H,m), 4.60-4.90 (4H,m), 4.90-5.60 (5H,m), 5.60-6.20 (5H,m), 6.78 (1H,d,J=15Hz)

b) Fifty mg (0.0962 mmol) of the compound prepared in the above reaction a) was dissolved in 1 ml of dichloromethane, and 0.01 ml (0.553 mmol) of water was added to the solution, which was cooled with ice under a nitrogen atmosphere. To this solution was added 2 mg (0.00285 mmol) of bis(triphenylphosphine)palladium (II) chloride and 0.12 ml (0.446 mmol) of tri-n-butyltin hydride, and the mixture was stirred for 5 minutes under ice-cooling, and then for 45 minutes at room temperature. To the mixture were added water and dichloromethane, and the aqueous layer was separated. The aqueous layer was washed with dichloromethane and concentrated. The residue was purified by reversal phase silica gel column chromatography (Chemco LC-SORB ®, SP-B-ODS, elution with 10-15% methanol - water), and lyophilized to give 7 mg (yield: 18%) of the title compound.

IR (KBr) cm$^{-1}$: 3320, 1755, 1690, 1615, 1575, 1390, 1280

UV$\lambda_{max}$ (0.1 M 3-morpholinopropanesulfonate buffer, pH 7.0): 296 nm ($\epsilon$=7,300)

NMR (D$_2$O) $\delta$: 1.11 (3H,d,J=7Hz), 1.19 (3H,d,J=6Hz), 1.80-2.20 (4H,m), 3.10-3.50 (3H,m), 3.60-3.80 (1H,m), 3.80-4.00 (1H,m), 4.00-4.20 (2H,m), 4.30-4.50 (1H,m), 6.21 (1H,d,J=16Hz), 6.66 (1H,dd,J=8.16Hz)

EXAMPLE 7

(5R,6S)-2-[(2R,5S)-2-(trans-2-Carbamoylvinyl)piperidin-5-yl]-thio-6-[(1R)-1-hydroxyethyl]-1-carbapen-2-em-3-carboxylic Acid

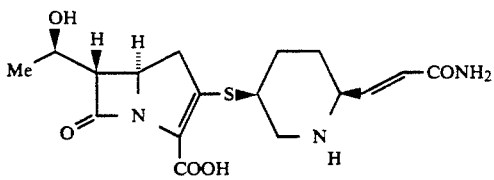

Thirty-nine mg (yield: 65%) of the title compound was obtained from (2S,5S)-1-allyloxycarbonyl-2-(trans-2-carbamoylvinyl)-5-mercaptopiperidine and 130 mg of allyl (5R,6S)-2-diphenylphosphoryloxy-6-[(1R)-1-hydroxyethyl]-1-carbapen-2-em -3-carboxylate in the same manner as in Example 6.

IR (KBr) cm$^{-1}$: 3410, 1740, 1690, 1650, 1620, 1575, 1400, 1150

UV $\lambda_{max}$ (0.1 M 3-morpholinopropanesulfonate buffer, pH 7.0): 297 nm ($\epsilon$ = 5,800)

NMR (D$_2$O) δ: 1.25 (3H,d,J=7Hz), 2.20–2.60 (4H,m), 2.90–3.40 (4H,m), 3.50–3.90 (2H,m), 4.00–4.20 (2H,m), 4.30–4.50 (1H,m), 6.20 (1H, dd,J=2.16Hz), 6.75 (1H,dd,J=7,16Hz)

EXAMPLE 8

(2S,5S)-2-Dimethylcarbamoyl-5-mercapto-1-p-nitrobenzyloxycarbonylpiperidine

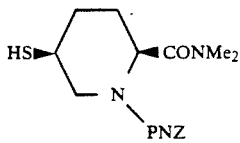

EXAMPLE 8-(1)

(2S,5R)-5-Hydroxy-2-methylcarbonyl-1-p-nitrobenzyloxycarbonylpiperidine

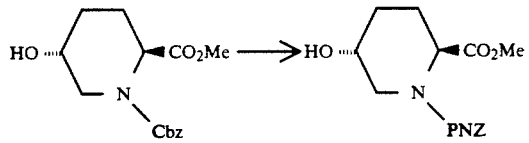

To a solution of 5.7 g (19.43 mmol) of (2S,5R)-1-benzyloxycarbonyl-5-hydroxy-2-methoxycarbonylpiperidine, which was prepared by the procedure described in P.D. Bailey et al., Tetrahedron Letters. 29, 2231 (1988), in 250 ml of methanol was added 570 mg of 5% palladium-carbon, and the mixture was hydrogenated at atmospheric pressure and room temperature for 1 hours. The catalyst was removed by filtration, and the solvent was removed. To a solution of this residue in 30 ml of dioxane was dropwise added a solution of 6.85 g (21.45 mmol) of p-nitrobenzyloxycarbonyl-4,6-dimethyl-2-mercaptopyrimidine in 50 ml of dioxane, and the mixture was stirred for 1.5 hours at room temperature. To the reaction mixture was added 300 ml of ethyl acetate, the organic layer was washed successively with 50 ml of 1N HCl(×2), 50 ml of water and saturated aqueous sodium chloride. After the extract was dried over anhydrous sodium sulfate, the solvent was removed. The residue was purified by silica gel column chromatography (Wakogel® C-300, elution with ethyl acetate - hexane system) to give 5.81 g (yield: 88%) of the title compound.

IR (KBr) cm$^{-1}$: 3500, 1740, 1700, 1520, 1430

NMR (CDCl$_3$) δ: 1.40–2.50 (4H,m), 3.10–3.40 (2H,m), 3.84 (3H,s), 4.00–4.40 (2H,m), 4.90–5.10 (1H,dd,J=4.14Hz), 5.10–5.50 (2H,m), 7.49 and 7.54 (2H, each d, J=8Hz), 8.24 (2H,d,J=8Hz)

EXAMPLE 8-(2)

(2S,5R)-5-Hydroxy-2-p-methoxybenzyloxycarbonyl-1-p-nitrobenzyloxycarbonylpiperidine

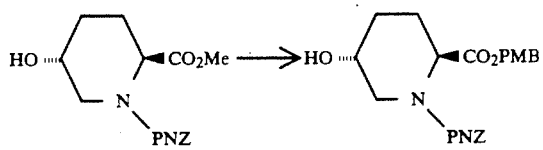

To a solution of 5.58 g (16.49 mmol) of the compound prepared in Example 8-(1) in 50 ml of methanol was added 25 ml (25 mmol) of 1N NaOH under ice-cooling, and the solution was stirred for 5 hours at room temperature. To the reaction mixture was added 25 ml (25 mmol) of 1N HCl under ice-cooling, and the mixture was concentrated to remove methanol. The resulting aqueous solution was extracted with 300 ml of ethyl acetate. The organic layer was separated and washed with 50 ml of water (×2) followed by saturated aqueous sodium chloride. After the extract was dried over anhydrous sodium sulfate, the solvent was removed. To a solution of this residue in 50 ml of DMF was added 4.83 g (34.65 mmol) of triethylamine, then 4.48 ml (33 mmol) of p-methoxybenzyl chloride. The mixture was stirred overnight at 70° C., and poured into 300 ml of ice-water. The mixture was extracted three times with ethyl acetate (200 ml×1, 100 ml×2), and the organic layer was washed with 200 ml of water (×2) followed by saturated aqueous sodium chloride. The extract was dried over anhydrous sodium sulfate and the solvent was removed. The residue was purified by silica gel column chromatography (Wakogel® C-300, elution with ethyl acetate - hexane system) to give 5.32 g (yield: 73%) of the title compound.

IR (KBr) cm$^{-1}$: 3450, 1730, 1680, 1610, 1510

NMR (CDCL$_3$) δ:1.40–2.40 (4H m) 3.10–3.40 (2H m) 3.82 (3H,s), 3.90–4.20 (2H,m), 4.90–5.10 (1H,m), 5.10–5.40 (4H,m), 5.15 (3H,s), 6.88 (2H,d,J=8Hz), 7.27 (2H,d,J=8Hz), 7.37 and 7.49 (2H, each d, J=8Hz), 8.13 and 8.20 (2H, each d, J=8Hz)

EXAMPLE 8-(3)

(2S,5S)-5-Acetylthio-2-p-methoxybenzyloxycarbonyl-1-p-nitrobenzyloxycarbonylpiperidine

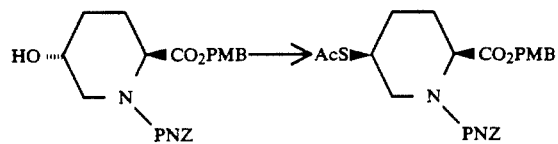

To a solution of 5.45 g (12.26 mmol) of the compound prepared in Example 8-(2) in 20 ml of THF was added 6.43 g (24.51 mmol) of triphenylphosphine, and the solution was cooled with ice under nitrogen atmosphere. To this solution was slowly added dropwise 3.9 ml (24.49 mmol) of diethyl azodicarboxylate, and the mixture was stirred for 30 minutes at the same temperature. To the mixture was added 1.85 ml (25.88 mmol) of thioacetic acid, and the mixture was stirred for 1 hour under ice-cooling followed by overnight at room temperature. The solvent was removed and the residue was purified by silica gel column chromatography (Wakogel ® C-300, elution with ethyl acetate - dichloromethane - hexane system) to give 4.53 g (yield: 74%) of the title compound.

IR (KBr) cm$^{-1}$: 1730, 1710, 1610, 1520, 1350

NMR (CDCl$_3$) δ: 1.20–2.10 (4H,m), 2.34 (3H,s), 3.30–3.60 (2H,m), 3.82 (3H,s), 3.90–4.20 (2H,m), 4.90–5.10 4.80–5.10 (1H,m), 5.10–5.40 (4H,m), 5.15 (3H,s), 6.88 (3H,s), 6.90 (2H,d,J=8Hz), 7.27 (2H,d,J=8Hz), 7.37 and J=8Hz), 7.36 and 7.54 (2H, each d, J=8Hz), 8.13 and 8.23 (2H, each d, J=8Hz)

EXAMPLE 8-(4)

(2S,5S)-5-Acetylthio-2-dimethylcarbamoyl-1-p-nitrobenzyloxycarbonylpiperidine

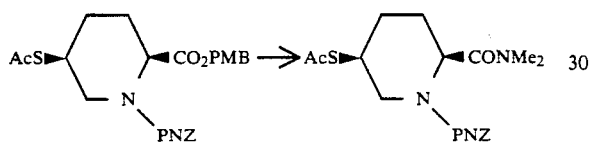

To a solution of 3.4 g (6.77 mmol) of the compound prepared in Example 8-(3) in 20 ml of dichloromethane was added 2 ml of anisole followed by 20 ml of trifluoroacetic acid. After stirring for 30 minutes at room temperature, trifluoroacetic acid in the mixture was removed in vacuo. The residue was purified by silica gel column chromatography (Wakogel ® C-300, elution with methanol - chloroform system) to give the corresponding carboxylic acid. To a solution of this acid in 25 ml of THF were added 900 mg (11 mmol) of dimethylamine hydrochloride and 1.44 g (11.8 mmol) of 4-dimethylaminopyridine. To the mixture was dropwise added a solution of 2.52 g (12.2 mmol) of DCC in THF (5 ml), and the mixture was stirred overnight at room temperature. To the reaction mixture was added 300 ml of ethyl acetate and 50 ml of 1N HCl, and the resulting insoluble matter was removed by filtration. The organic layer was separated and washed with 50 ml of water followed by saturated aqueous sodium chloride. The extract was dried over anhydrous sodium sulfate, and the solvent was removed. The residue was purified by silica gel column chromatography (Wakogel ® C-300, elution with ethyl acetate—dichloromethane system), and crystallized from ethyl acetate—hexane to give 720 mg (yield: 26%) of the title compound.

mP: 113–114° C.

IR (KBr) cm$^{-1}$: 1700, 1690, 1640, 1510, 1340

NMR (DDCl$_3$)δ: 1.70–2.10 (4H,m), 2.35 (3H,s), 2.95 (3H,s), 3.07 (3H,s), 3.30–3.60 (2H,m), 4.10–4.30 (1H,m), 5.00–5.20 (1H,m), 5.22 and 5.32 (2H,ABq,J=14Hz), 7.58 (2H,d, J=8Hz), 8.25 (2H,d,J=8Hz)

[d]$^{25}_D$ −50.9° (C=1,MeOH)

EXAMPLE 8-(5)

(2S,5S)-2-Dimethylcarbamoyl-5-mercapto-1-p-nitrobenzyloxycarbonylpiperidine

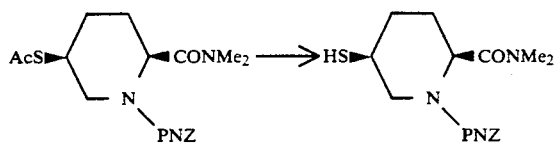

To a solution of 730 mg (1.78 mmol) of the compound prepared in Example 8(4) in 73 ml of methanol was added 1.79 ml (1.79 mmol) of 1N NaOH at room temperature under a nitrogen atmosphere and the mixture was stirred for 20 minutes. To the mixture was added 1.97 ml (1.97 mmol) of 1N HCl, and methanol in the mixture was removed. To the residue was added 200 ml of ethyl acetate and 25 ml of water. The organic layer was separated, washed with 25 ml of water, and dried over anhydrous sodium sulfate. The solvent was removed to give the title compound, which was used in the reaction of Example 1 without purification.

EXAMPLE 9

(2S,5S)-5-Mercapto-2-methylcarbamoyl-1-p-nitrobenzyloxycarbonylpiperidine

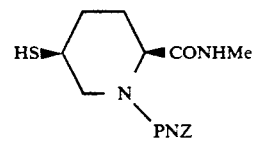

EXAMPLE 9-(1)

2S,5R 1-5-Hydroxy-1,2-bis(p-nitrobenzyloxycarbonyl)-piperidine

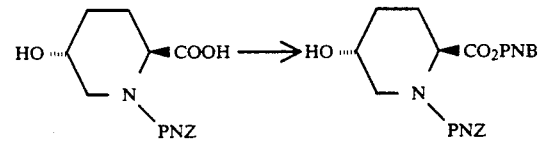

To a solution of 1.71 g (5.27 mmol) of (2S,5R)-2-carboxy-5-hydroxy-1-p-nitrobenzyloxycarbonylpiperidine in DMF (16 ml) was added 1.47 ml (10.55 mmol) of triethylamine followed by 1.0 g (5.8 mmol) of p-nitrobenzyl chloride, and the mixture was stirred overnight at 70–80° C. The reaction mixture was poured into ice-water, and extracted with ethyl acetate. The organic layer was washed with water, and dried over anhydrous sodium sulfate. The solvent was removed, and the residue was purified by silica gel column chromatography (Wakogel ® C-300, elution with ethyl acetate - dichloromethane system) to give 2.04 g (yield: 84%) of the title compound.

IR (KBr) cm$^{-1}$: 3470, 2950, 1740, 1700, 1610, 1520, 1350

NMR (CDCl$_3$) δ: 1:35–1.60 (1 H,m), 1.60–1.90 (2H,m), 1.95–2.20 (1 H,m), 2.20–2.40 (1H,m), 3.15–3.40 (1 H,m), 3.95–4.15 (2H,m), 4.95–5.15 (1 H,m), 5.15–5.50 (4H,m), 7.40–7.80 (4H,m), 8.10–8.50 (4H,m)

EXAMPLE 9-(2)
(2S,5S)-5-Ethoxycarbonylthio-1,2-bis(p-nitrobenzyloxycarbonyl)-piperidine

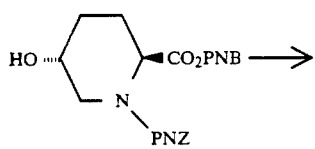

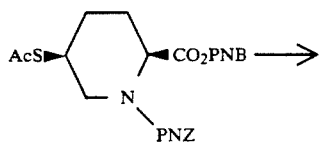

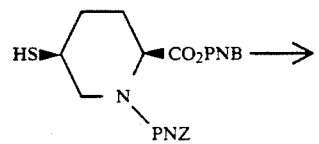

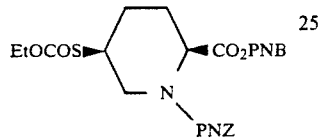

To a solution of 1.95 g (4.24 mmol) of the compound prepared in Example 9-(1) in 8 ml of THF was added 2.23 g (8.50 mmol) of triphenylphosphine, and the solution was cooled with ice under a nitrogen atmosphere. To the mixture was slowly dropwise added 1.35 ml (8.48 mmol) of diethyl azodicarboxylate and the mixture was stirred for 30 minutes at the same temperature. To the mixture was additionally added 0.62 ml (8.67 mmol) of thioacetic acid, and the mixture was stirred for 1 hour under ice-cooling followed by overnight at room temperature. The solvent was removed, and the residue was purified by silica gel column chromatography (Wakogel® C-300, elution with ethyl acetate - hexane system) to give 1.25 g of (2S,5S)-5-acetylthio-1,2-bis(p-nitrobenzyloxycarbonyl)piperidine at a crude product. To a solution of 1.01 g of this product in 80 ml of methanol was dropwise added 1.96 ml of 1N NaOH under ice-cooling and a nitrogen atmosphere, and the mixture was stirred for 20 minutes at room temperature. The reaction mixture was neutralized with 1N HCl, and methanol in the mixture was removed in vacuo. To the mixture was added 200 ml of ethyl acetate, and the organic layer was separated, washed with water and dried over anhydrous sodium sulfate. The solvent was removed and the residue was dissolved in 25 ml of THF. To this solution was dropwise added 0.33 ml (2.37 mmol) of triethylamine followed by 0.28 ml (2.93 mmol) of ethyl chloroformate under ice-cooling and a nitrogen atmosphere. After stirring for 1 hour under ice-cooling, 0.1 ml (0.79 mmol) of triethylamine and 0.1 ml (1.05 mmol) of ethyl chloroformate were additionally added to the mixture, which was stirred for 1 hour at the same temperature. To the mixture was added 150 ml of ethyl acetate, and the organic layer was washed successively with 1N HCl, water and saturated aqueous sodium chloride. After drying over anhydrous sodium sulfate, the solvent was removed, and the residue was purified by silica gel column chromatography (Wakogel® C-300, elution with ethyl acetate - hexane system) to give 630 mg (yield: 34%) of the title compound.

IR (KBr) cm$^{-1}$ 1740, 1705, 1600, 1345, 1145

NMR (CDCl$_3$) δ: 1.10-1.40 (3H,m), 1.50-2.50 (4H,m), 2.90-3.20 (1H,m), 3.20-3.50 (1H,m), 4.00-4.50 (3H,m), 4.80-5.30 (3H,m), 5.30 (2H,s), 7.40-7.80 (4H,m), 8.10-8.40 (4H,m)

EXAMPLE 9-(3)
2S,5S)-5-Ethoxycarbonylthio-2-methylcarbamoyl-1-p-nitrobenzyloxycarbonylpiperidin

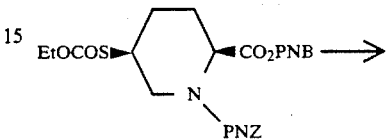

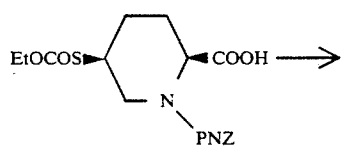

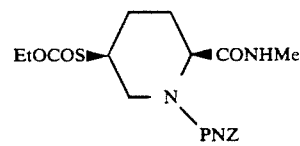

To a solution of 600 mg (1.1 mmol) of the compound prepared in Example 9-(2) in 22 ml of 50% aqueous THF was dropwise added 1.15 ml (1.15 mol) of 1N NaOH at room temperature, and the mixture was stirred for 3 hours. After neutralization with 1N HCl, THF in the mixture was removed in vacuo. The resulting aqueous solution was extracted with ethyl acetate, and the organic layer was washed with water, and then dried over anhydrous sodium sulfate. The solvent was removed, and the residue was purified by silica gel column chromatography (Wakogel® C-300, elution with methanol - chloroform system) to give 250 mg (yield: 55%) of the corresponding carboxylic acid. To a solution of this acid in 10 ml of THF was slowly dropwise added 0.17 ml (1.22 mmol) of triethylamine followed by 0.12 ml (1.26 mmol) of ethyl chloroformate under ice-cooling and a nitrogen atmosphere. After stirring for 15 minutes under ice-cooling, 4.5 ml of 40% aqueous methylamine was dropwise added to the mixture, which was stirred for 30 minutes at the same temperature. To the mixture was added 150 ml of ethyl acetate, and the organic layer was washed successively with 1N HCl, water and saturated aqueous sodium chloride. After drying over anhydrous sodium sulfate, the solvent was removed. The residue was purified by silica gel column chromatography (Wakogel® C-300, elution with methanol-chloroform system) to give 110 mg (yield: 43%) of the title compound.

IR (KBr) cm$^{-1}$: 1705, 1660, 1610, 1520, 1350, 1160

NMR (CDCl$_3$) δ: 1.27 (3H,t,J=7Hz), 1.40-2.20 (4H,m), 2.30-2.60 (1H,m), 2.60-3.10 (1H,m), 2.85 (3H,d,J=5Hz), 4.31 (2H,q,J=7Hz), 4.30-4.60 (1H,m), 4.70-4.90 (1H,m), 5.30 (2H,s), 5.90-6.20 (1H,s), 7.40-7.70 (2H,m), 8.26 (2H,d,J=9Hz)

EXAMPLE 9-(4)

(2S,5S)-5-Mercapto-methylcarbamoyl-1-p-nitrobenzyloxycarbonylpiperidine

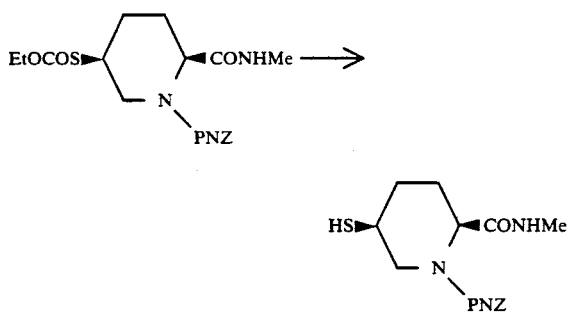

To a solution of 160 mg (0.376 mmol) of the compound prepared in Example 9-(3) in 8 ml of 50% aqueous methanol was dropwise added 0.47 ml (0.47 mmol) of 1N NaOH at room temperature under a nitrogen atmosphere, and the mixture was stirred for 30 minutes. After neutralization with 1N HCl, methanol in the mixture was removed. The resulting aqueous solution was extracted with ethyl acetate, and the organic layer was washed with water, and then dried over anhydrous sodium sulfate. The solvent was removed to give the title compound which was used in the reaction of Example 5 without purification.

EXAMPLE 10

(2R,5S)-1-Allyloxycarbonyl-2-(trans-2-carbamoylvinyl)-5-mercaptopiperidine

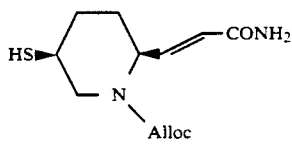

EXAMPLE 10-(1)

(2S,5R)-1-Allyloxycarbonyl-5-hydroxy-2-methoxycarbonylpiperidine

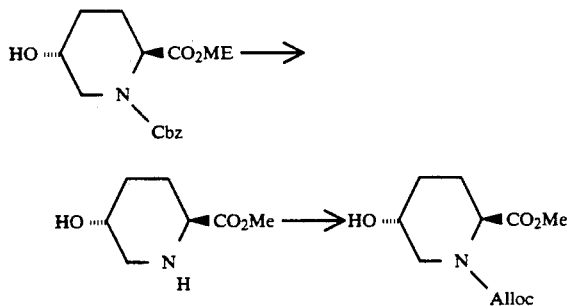

To a solution of 2.46 g (8.39 mmol) of (2S,5R)-1-benzyloxycarbonyl-5-hydroxy-2-methoxycarbonylpiperidine in 100 ml of methanol was added 500 mg of 5% palladium-carbon, and the mixture was hydrogenated for 2 hours at atmospheric pressure and room temperature. The catalyst was removed by filtration, and the filtrate was concentrated. The residue was dissolved in 20 ml of dichloromethane. To this solution was dropwise added 1.3 ml (9.33 mmol) or triethylamine followed by 0.98 ml (9.24 mmol) of allyl chloroformate. After stirring for 2 hours, 1.3 ml (9.33 mmol) of triethylamine and 0.98 ml (9.24 mmol) of allyl chloroformate were additionally added to the mixtures, which was stirred for 1 hours. To the mixture was added 200 ml of ethyl acetate, the organic layer was washed successively with water, 1N potassium bisulfate, water, saturated aqueous sodium bicarbonate, water and saturated aqueous sodium chloride. After drying over anhydrous sodium sulfate, the solvent was removed. The residue was purified by silica gel column chromatography (Wakogel ®C-300, elution with ethyl acetate - hexane system) to give 1.14 g (yield: 55%) of the title compound.

IR (KBr) cm$^{-1}$: 3500, 2950, 1745, 1700, 1440, 1420 1250, 1130, 1020

NMR (CDCl$_3$) δ: 1.10–2.40 (4H,m), 3.10–3.30 (1H,m), 3.74 (3H,s), 3.90–4.30 (3H,m), 4.50–4.80 (2H,m), 4.90–5.10 (1H,m), 5.10–5.50 (2H,m), 5.80–6.10 (1H,m)

EXAMPLE 10-(2)

(2S,5S)-1-Allyloxycarbonyl-5-mesyloxy-2-methoxycarbonylpiperidine

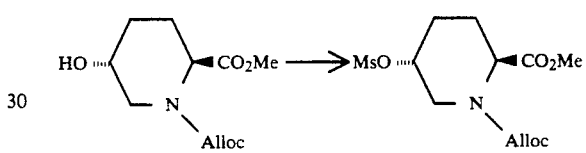

To a solution of 1.14 g (4.69mmol) of the compound prepared in Example 10-1) in 15 ml of THF was dropwise added 1.3 ml (9.33 mmol) of triethylamine followed by 0.55 ml (7.11 mmol) of methanesulfonyl chloride under ice-cooling, and the mixture was stirred for 1 hour at the same temperature and then for 30 minutes at room temperature. To the mixture was added 150 ml of ethyl acetate, and the organic layer was washed successively with 1N potassium bisulfate, water, and saturated aqueous sodium chloride. After drying over anhydrous sodium sulfate, the solvent was removed. The residue was purified by silica gel column chromatography (Wakogel ® C-300, elution with ethyl acetate - hexane system) to give 1.49 g (yield: 99%) of the title compound.

IR (KBr) cm$^{-1}$: 2950, 1740, 1705, 1440, 1420, 1355 1340, 1250, 1175, 910

NMR (CDCl$_3$) δ: 1.50–1.80 (1H,m), 2.00–2.40 (3H,m), 3.04 and 3.08 (3H,s), 3.20–3.50 (2H,m), 3.76 (3H,s), 4.30–4.50 (1H,m), 450–4.80 (2H,m), 4.80–5.10 (1H,m), 5.10–5.55 (2H,m), 5.80–6.10 (1H,m)

EXAMPLE 10-(3)

(2S,5S)-1-Allyloxycarbonyl-2-methoxycarbonyl-5-tritylthiopiperidine

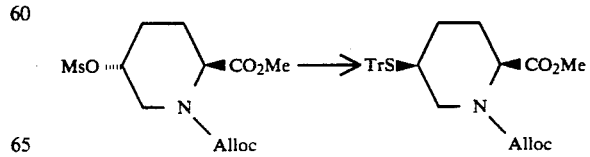

To a solution of 1.38 g (4.99 mmol) of tritylmercaptan in 7 ml of DMF was added 190 mg (4.75 mmol) of 60% sodium hydride in oil under ice-cooling and a nitrogen atmosphere, and the mixture was stirred for 10 minutes. To this mixture was added a solution of 1.46 g (4.54 mmol) of the compound prepared in Example 10-(2) in 5 ml of DMF, and the mixture was stirred overnight. The reaction mixture was poured into 120 ml of ice-water containing a solution of 10 ml of 1N potassium bisulfate, and the resulting mixture was extracted with ethyl acetate. The organic layer was washed with water, and dried over anhydrous sodium sulfate. The solvent was removed, and the residue was purified by silica gel column chromatography (Wakogel ® C-300, elution with ethyl acetate - hexane system) to give 880 mg (yield: 39%) of the title compound.

IR (KBr) cm$^{-1}$: 2950, 1750, 1710, 1490, 1450, 1410, 1210, 1150, 1010

NMR (CDCl$_3$) δ: 1.00–1.80 (4H,m), 1.90–2.40 (1H,m), 2.40–2.90 (1H,m), 3.40–4.30 (4H,m), 4.40–4.90 (3H,m), 5.00–5.50 (2H,m), 5.70–6.10 (1H,m), 7.00–8.00 (15H,m)

EXAMPLE 10-(4)

(2S,5S)-1-Allyloxycarbonyl-2-hydroxymethyl-5-tritylthiopiperidine

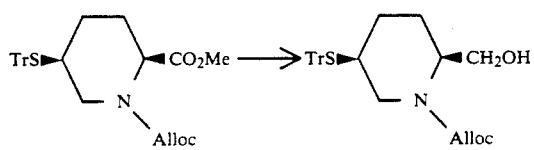

To a solution of 420 mg (0.837 mmol) of the compound prepared in Example 10-3) in 2 ml of THF was added 71 mg (1.67 mmol) of lithium chloride followed by 63 mg (1.67 mmol) of sodium borohydride and then 2 ml of ethanol at room temperature under a nitrogen atmosphere, and the mixture was stirred overnight at room temperature. The reaction mixture was acidified with 10% aqueous citric acid under ice-cooling, and the organic solvent in the mixture was removed. The resulting aqueous solution was extracted with ethyl acetate, and the organic layer was washed with water, and dried over anhydrous sodium sulfate. The solvent was removed, and the residue was purified by silica gel column chromatography (Wakogel ® C-300, elution with ethyl acetate - hexane system) to give 280 mg (yield: 71%) of the title compound.

IR (KBr) cm$^{-1}$: 3420, 2940, 1690, 1445, 1415, 1265

NMR (CDCl$_3$) δ: 1.00–2.00 (5H,m), 2.00–2.30 (1H,m), 2.60–2.90 (1H,m), 3.30–4.00 (3H,m), 4.10–4.30 (1H,m), 4.30–4.80 (2H,m), 5.10–5.40 (2H,m), 5.70–6.10 (1H,m), 7.00–8.00 (15H,m)

EXAMPLE 10-(5)

(2R,5S)-1-Allyloxycarbonyl-2-(trans-2-carbamoylvinyl)-5-tritylthiopiperidine

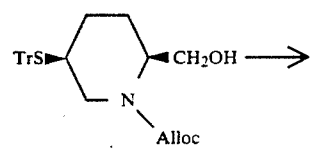

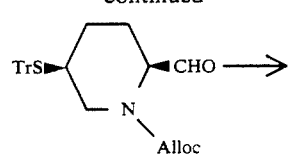

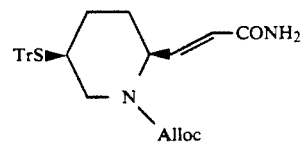

To a solution of 0.1 ml (1.41 mmol) of dimethyl sulfoxide in 1.5 ml of dichloromethane was dropwise added 0.06 ml (0.688 mmol) of oxalyl chloride at −78° C. under a nitrogen atmosphere, and the mixture was stirred for 30 minutes. To this mixture was slowly added a solution, precooled to −78° C., of 220 mg (0.464 mmol) of the compound prepared in Example 10-(4) in dichloromethane (1 ml). After stirring for 30 minutes, 0.32 ml (2.3 mmol) of triethylamine was dropwise added to the mixture, which was stirred for 10 minutes at −78° C., and then for 1 hour at room temperature. To the mixture was added 30 ml of dichloromethane, and the organic layer was washed with 1N potassium bisulfate followed by water. After drying over anhydrous sodium sulfate, the solvent was removed. To a solution of 130 mg (0.666 mmol) of diethyl carbamoylmethylphosphonate in 1.5 ml of THF was added 24 mg (0.6 mmol) of 60% sodium hydride in oil under ice-cooling and a nitrogen atmosphere, and the mixture was stirred for 30 minutes. To this solution was added a solution of the above residue in THF (1 ml), and the mixture was stirred for 30 minutes under ice-cooling. To the mixture was added 30 ml of ethyl acetate, and the organic layer was washed with water. After drying over anhydrous sodium sulfate, the solvent was removed. The residue was purified by silica gel column chromatography (Wakogel ® C-300, elution with methanol - chloroform system) to give 160 mg (yield: 67%) of the title compound.

IR (KBr) cm$^{-1}$: 3400, 2930, 1680

NMR (CDCl$_3$)δ: 1.20–2.00 (4H,m), 2.00–2.40 (1H,m), 2.50–2.90 (1H,m), 3.60–4.00 (1H,m), 4.40–4.80 (2H,m), 4.80–5.00 (1H,m), 5.10–5.40 (2H,m), 5.50–6.20 (4H,m), 6.73 (1H,dd,J=5, 15Hz), 7.10–8.10 (15H,m)

EXAMPLE 10-(6)

(2R,5S)-1-Allyloxycarbonyl-2-(trans-2-carbamoylvinyl)-5mercaptopiperidine

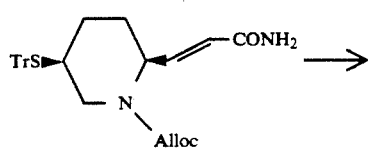

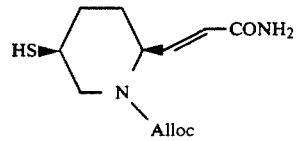

To a solution of 140 mg (0.273 mmol) of the compound prepared in Example 10-(5) in 0.5 ml of dichloromethane under ice-cooling and a nitrogen atmosphere was dropwise added 0.5 ml of trifluoroacetic acid followed by 0.05 ml (0.313 mmol) of triethylsilane, and the mixture was stirred for 20 minutes under ice-cooling followed by 30 minutes at room temperature. The solvent was removed, and the residue was dissolved in 30 ml of ethyl acetate. The solution was washed with 1M phosphate buffer (pH 5.5) followed by saturated aqueous sodium chloride. After drying over anhydrous sodium sulfate, the solvent was removed. The residue was purified by silica gel column chromatography (Wakogel ® C-300, elution with methanol - dichloromethane system) to give 70 mg (yield: 95%) of the title compound, which was used in the reaction of Example 6.

EXAMPLE 11

(2S,5S)-2-Carbamoyl-5-mercapto-1-p-nitrobenzyloxycarbonylpiperidine

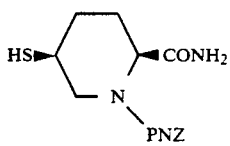

EXAMPLE 11-(1)

(2S,5R)-2-Carbamoyl-5-mesyloxy-1-p-nitrobenzyloxycarbonylpiperidine

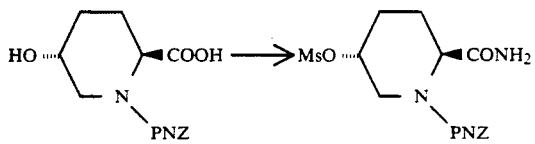

To a solution of 490 mg (1.51 mmol) of (2S,5R)-2-carboxy-5-hydroxy-1-p-nitrobenzyloxycarbonylpiperidine, which was prepared from the compound of Example 8-2) by a conventional method for the deprotection, in 8 ml of THF was dropwise added 0.23 ml (1.65 mmol) of triethylamine followed by 0.16 ml (1.67 mmol) of ethyl chloroformate at −30° C., and the mixture was stirred for 50 minutes at the same temperature. The mixture was cooled to −40° C., and 1.5 ml of concentrated aqueous ammonia was dropwise added. The reaction mixture was gradually warmed to room temperature and then stirred for 1 hour. The solvent was removed, and the residue was purified by silica gel column chromatography (Wakogel ® C-300, elution with methanol - chloroform system). To a solution of the resulting compound in 10 ml of THF was dropwise added 0.47 ml (3.37 mmol) of triethylamine followed by 0.26 ml (3.36 mmol) of mesyl chloride, and the mixture was stirred for 2 hours at room temperature. The solvent was removed, and the residue was purified by silica gel column chromatography (Wakogel ® C-300, elution with methanol - chloroform system) to give 430 mg (yield: 71%) of the title compound.

IR (KBr) cm$^{-1}$: 3420, 3150, 1700, 1515, 1345, 1175

NMR (DMSO-d$_6$) δ: 1.50-2.20 (4H,m), 3.20 (3H,s), 3.30-3.60 (2H,m), 4.50-4.30 (1H,m), 4.85-5.00 (1H,m), 5.23 and 5.35 (2H,ABq,J=14Hz), 7.24 (1H,br s), 7.57 (1H,br s), 7.55-7.75 (2H,m), 8.23 (2H,d,J=8Hz)

EXAMPLE 11-(2)

(2S,5S)-5-Acetylthio-2-carbamoyl-1-p-nitrobenzyloxycarbonylpiperidine

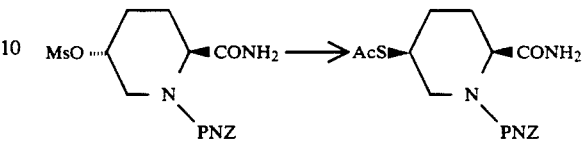

To a suspension of 60 mg (1.25 mmol) of 50% sodium hydride in oil in 4 ml of DMF was added 0.1 ml (1.4 mmol) of thioacetic acid under a nitrogen atmosphere, and the mixture was stirred for 25 minutes at room temperature. To the mixture was added 150 mg (1 mmol) of sodium iodide followed by a solution of 400 mg (1 mmol) of the compound prepared in Example 11-(1) in DMF (2 ml), and the mixture was stirred for 24 hours at 80-90° C. The reaction mixture was poured into 50 ml of cold aqueous sodium chloride, and extracted three times with 20 ml of benzene. The organic layer was washed with 10% aqueous sodium sulfite followed by saturated aqueous sodium chloride, and dried over anhydrous sodium sulfate. The solvent was removed, and the residue was purified by silica gel column chromatography (Wakogel ® C-300, elution with methanol chloroform system) to give 180 mg (yield: 47%) of the title compound as an oil.

IR (KBr) cm$^{-1}$: 3400, 3200, 1710, 1680, 1520, 1350

NMR (CDCl$_3$) δ: 1.60-2.10 (4H,m), 2.34 (3H,s), 2.80-3.10 (1H,m), 3.30-3.60 (1H,m), 4.25-4.45 (1H,m), 4.75-5.00 (1H,m), 5.26 and 5.38 (2H,ABq,J=14Hz), 5.72 (1H,br s), 6.03 (1H,br s), 7.45-7.80 (2H,m), 8.27 (2H,d, J=8Hz)

EXAMPLE 11-(3)

(2S,5S)-2-Carbamoyl-5-mercapto-1-p-nitrobenzyloxycarbonylpiperidine

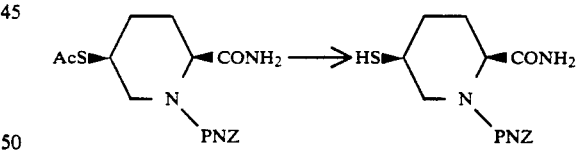

The title compound was obtained from the compound prepared in Example 11-2) in the same manner as in Example 8-(5). This compound was used in the next reaction without purification.

The compound of the general formula (I) according to the present invention has excellent antibacterial activity against both gram-positive and gram-negative bacteria and, as such, are very useful.

Furthermore, the compound (II) described herein is a novel compound which has not been described in the literature and is of value as a synthetic intermediate of compound (I).

While the invention has been described in detail and with reference to specific embodiments thereof, it will be apparent to one skilled in the art that various changes and modifications can be made therein without departing from the spirit and scope thereof.

What is claimed is:

1. A compound represented by the general formula (I):

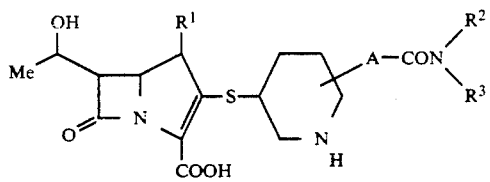

wherein R¹ is a hydrogen atom or a methyl group; R² and R³, which may be the same or different, each represents a hydrogen atom or a lower alkyl group, or taken together with the adjacent nitrogen atom, jointly represent a heterocyclic group selected from the group consisting of an aziridinyl group, an azetidinyl group, a pyrrolidinyl group, a piperidino group, a piperazinyl group, a 4-lower alkylpiperazinyl group, a morpholino group and a thiomorpholino group; and A is a single bond, a lower alkylene group, a lower alkenylene group or a lower alkynylene group; or a pharmaceutically acceptable salt or ester thereof.

2. The compound of claim 1, which has the general formula (I-a):

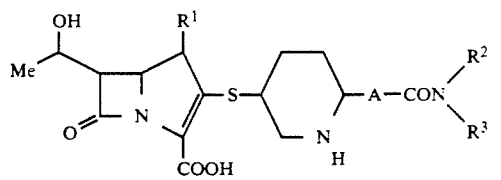

or the general formula (I-b):

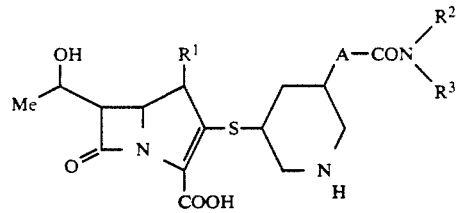

wherein R¹ is a hydrogen atom or a methyl group; R² and R³, which may be the same or different, each represents a hydrogen atom or a lower alkyl group, or taken together with the adjacent nitrogen atom, jointly represent a heterocyclic group selected from the group consisting of an aziridinyl group, an azetidinyl group, a pyrrolidinyl group, a piperidino group, a piperazinyl group, a 4-lower alkylpiperazinyl group, a morpholino group and a thiomorpholino group; and A is a single bond, a lower alkylene group, a lower alkenylene group or a lower alkynylene group.

3. The compound of claim 1, which has the general formula (I-a):

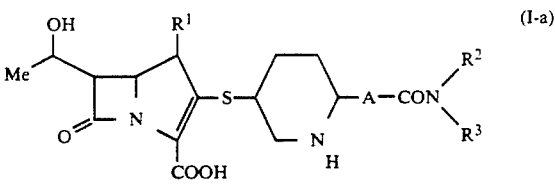

wherein R¹ is a hydrogen atom or a methyl group; R² and R³, which may be the same or different, each represents a hydrogen atom or a lower alkyl group, or taken together with the adjacent nitrogen atom, jointly represent a heterocyclic group selected from the group consisting of an aziridinyl group, an azetidinyl group, a pyrrolidinyl group, a piperidino group, a piperazinyl group, a 4-lower alkylpiperazinyl group, a morpholino group and a thiomorpholino group; and A is a single bond, a lower alkylene group, a lower alkenylene group or a lower alkynylene group.

4. The compound of claim 1, wherein R² and R³, which may be the same or different, each represents a hydrogen atom or a lower alkyl group.

5. The compound of claim 1, wherein A is a single bond or a lower alkenylene group.

6. The compound of claim 1, wherein the carbapenem skeleton has a (5R,6S,8R)-configuration or a (1R,5S,6S,8R)-configuration.

7. The compound of claim 1, which is selected from the group consisting of (5R,6S)-2-[(2S,5S)-2-dimethylcarbamoylpiperidin-5-yl]thio-6-[(1R)-1-hydroxyethyl]-1-carbapen-2-em-3-carboxylic acid, (5R,6S)-2-[(2S,5S)-2-carbamoylpiperidin-5-yl]thio-6-[(1R)-1hydroxyethyl]-1-carbapen-2-em-3-carboxylic acid, (5R,6S)-6-[(1R)-1-hydroxyethyl]-2-[(2S,5S)-2-methylcarbamoylpiperidin-5yl]thio-1-carbapen-2-em-3-carboxylic acid, (5R,6S)-2-[(2S,5S) -2-carbamoylvinylpiperidin-5-yl]thio-6-[(1R)-1-hydroxyethyl]-1-carbapen-2-em-3-carboxylic acid, (1R,5S,6S)-2-[(2S,5S)-2-dimethylcarbamoylpiperidin-5-yl]thio-6-[(1R)-1-hydroxyethyl]-1-methylcarbapen-2-em-3-carboxylic acid, (1R,5S,6S)-2-[(2S,5S) -2-carbamoylpiperidin-5-yl]thio-6-[(1R)-1-hydroxyethyl]-1-methylcarbapen-2-em-3-carboxylic acid, (1R,5S,6S)-6-[(1R)-1-hydroxyethyl]-2-[(2S,5S)-2-methylcarbamoylpiperidin-5-yl]thio -1-methylcarbapen-2-em-3-carboxylic acid and (1R,5S,6S)-2[(2S,5S)-2-carbamoylvinylpiperidin-5-yl]thio-6-[(1R)-1hydroxyethyl]-1-methylcarbapen-2-em-3-carboxylic acid.

8. The compound of claim 1, which is (1R,5S,6S) -2-[(2S,5S)-2-dimethylcarbamoylpiperidin-5-yl]thio-6-[(1R)-1-hydroxyethyl]-1-methylcarbapen-2-em-3-carboxylic acid.

9. An antibacterial composition comprising an effective amount of a compound represented by the general formula (I):

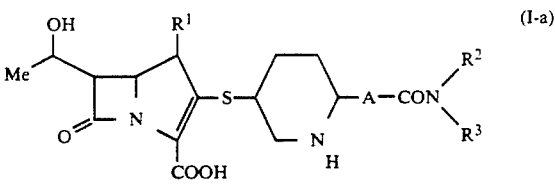

wherein R¹ is a hydrogen atom or a methyl group; R² and R³, which may be the same or different, each represents a hydrogen atom or a lower alkyl group, or taken together with the adjacent nitrogen atom, jointly represent a heterocyclic group selected from the group consisting of an aziridinyl group, an azetidinyl group, a pyrrolidinyl group, a piperidino group, a piperazinyl group, a 4-lower alkylpiperazinyl group, a morpholino group and a thiomorpholino group; and A is a single bond, a lower alkylene group, a lower alkenylene group or a lower alkynylene group; or a pharmaceutically acceptable salt or ester thereof.

* * * * *